United States Patent
Iwatschenko

(10) Patent No.: US 7,748,526 B2
(45) Date of Patent: Jul. 6, 2010

(54) MIXING DEVICE

(75) Inventor: Peter Iwatschenko, Neunkirchen (DE)

(73) Assignee: MTF MediTech Franken GmbH, Eckental (DE)

( * ) Notice: Subject to any disclaimer, the term of this patent is extended or adjusted under 35 U.S.C. 154(b) by 398 days.

(21) Appl. No.: 11/816,151

(22) PCT Filed: Feb. 8, 2006

(86) PCT No.: PCT/EP2006/001119

§ 371 (c)(1),
(2), (4) Date: Sep. 12, 2007

(87) PCT Pub. No.: WO2006/087128

PCT Pub. Date: Aug. 24, 2006

(65) Prior Publication Data

US 2008/0149502 A1     Jun. 26, 2008

(30) Foreign Application Priority Data

Feb. 15, 2005   (DE) .................. 10 2005 006 883

(51) Int. Cl.
   *B65D 25/08* (2006.01)
(52) U.S. Cl. ............. 206/219; 206/524.8; 433/90
(58) Field of Classification Search ......... 206/219–222, 206/524.8; 215/DIG. 8; 222/135, 136; 366/129, 366/130; 433/89, 90; 604/200, 201, 218
See application file for complete search history.

(56) References Cited

U.S. PATENT DOCUMENTS 3,028,052 A * 4/1962 Archer .................. 222/136
3,756,390 A * 9/1973 Abbey et al. ............. 206/219
5,026,283 A * 6/1991 Osanai et al. ............... 433/90
5,114,240 A * 5/1992 Kindt-Larsen et al. ...... 366/129
5,193,907 A    3/1993 Faccioli et al.
6,349,850 B1   2/2002 Cheikh
6,386,872 B1 * 5/2002 Mukasa et al. ............. 433/90
6,682,347 B2  1/2004 Aoyagi et al.
2001/0047162 A1 11/2001 Yugari
2002/0098462 A1 * 7/2002 Kaneko et al. ............. 433/89
2004/0104133 A1 6/2004 Aoyagi et al.

FOREIGN PATENT DOCUMENTS

| CH | 556270       | 11/1974 |
| EP | 0783872 A2   | 7/1997  |
| EP | 0380867 B1   | 8/1997  |
| EP | 1344500 A1   | 9/2003  |
| WO | 0023002 A1   | 4/2000  |
| WO | 2004082507 A1| 9/2004  |

* cited by examiner

*Primary Examiner*—Luan K Bui
(74) *Attorney, Agent, or Firm*—Robert R. Deleault, Esq.; Mesmer & Deleault, PLLC

(57) ABSTRACT

The invention relates to a mixing device with a first chamber (1) for a first component, in particular a powder [a liquid], a second chamber (12) for a second component, in particular a liquid [powder], and a divider means (11, 13) separating the first and the second chamber. The second chamber is defined by an inner hollow cylinder (10) which is arranged so as to be moved in a piston-like fashion in an outer hollow body (2) defining the first chamber. According to the invention, the first chamber comprises an evacuation opening (5) which is adapted to be connected with a vacuum source. The invention further relates to a method for vacuum packaging the mixing device.

12 Claims, 3 Drawing Sheets

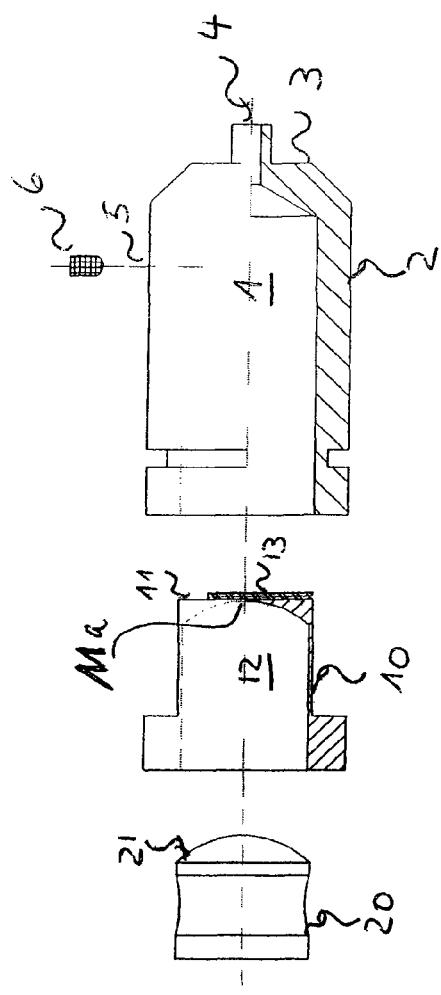
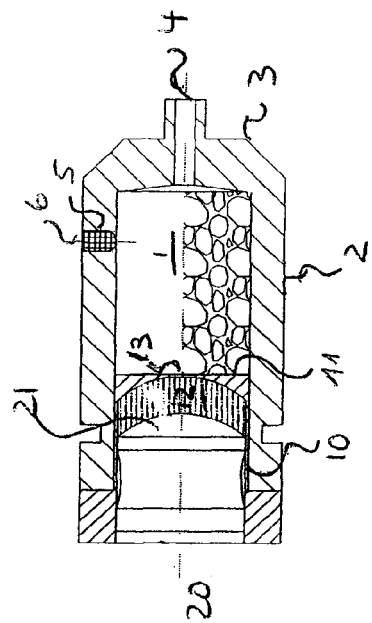
Fig. 1
Fig. 2

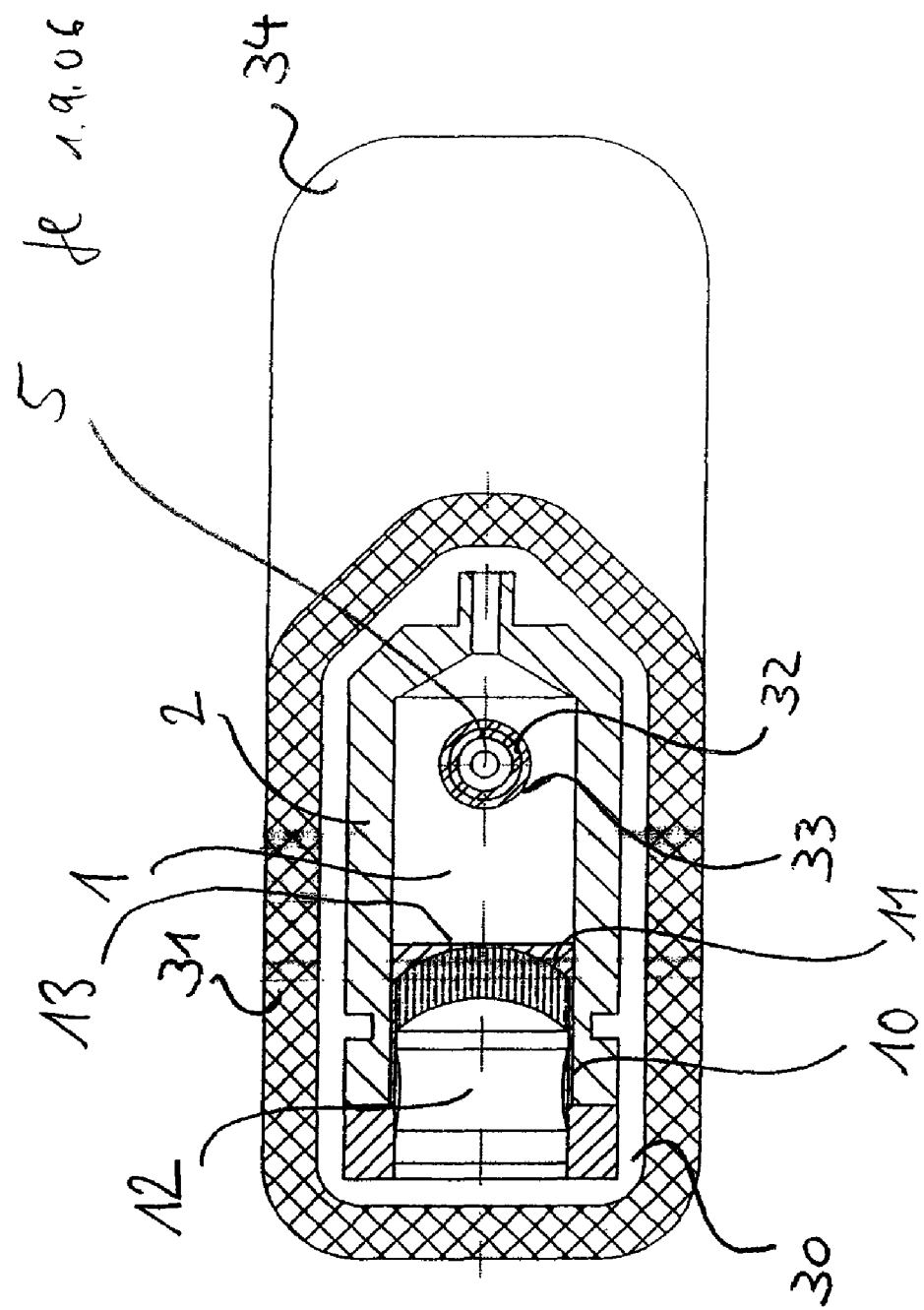

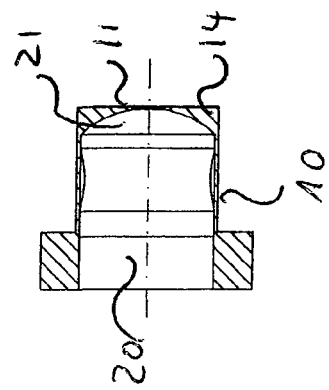
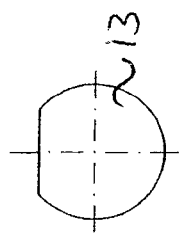
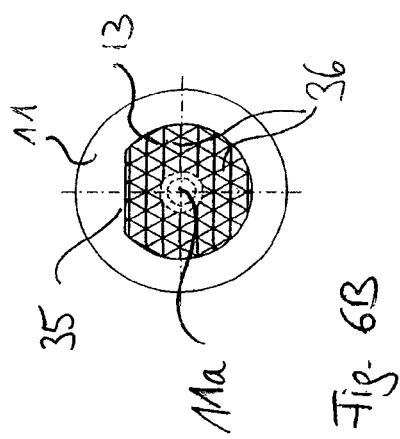
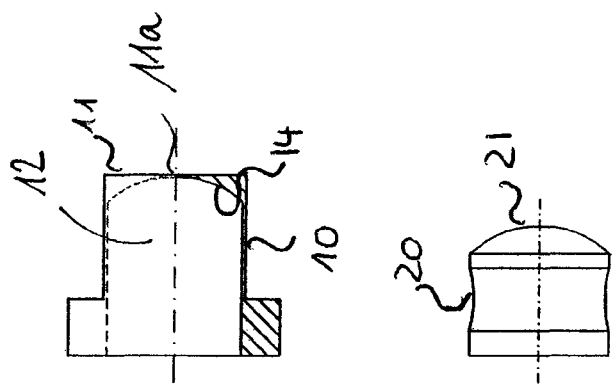
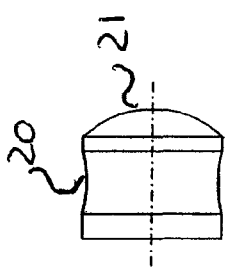

MIXING DEVICE

The invention relates to a mixing device for two components, in particular a liquid and a pulverised substance, as well as to a method for vacuum packaging the mixing device.

Devices for making mixtures of two or more components are known, in which the components have been filled by the manufacturer into different chambers which are separated from each other, and which are only brought in contact and mixed with each other by the user, for example, by destroying a wall separating the chambers. These are also referred to as multi-component mixing capsules.

In the medical field, such mixing devices are frequently used for making dental materials which are generally mixed from a pulverised and a liquid component, with the mixing operation usually being carried out by a mixing apparatus which generates shaking movements or vibrations that are transferred to a mixing device placed into the apparatus. The finish-mixed substance is then applied directly to the application site by means of an ejection aperture arranged at the mixing device. Such mixing devices are also employed for the manufacture of bone cements in orthopedic applications.

In the following the invention will be explained, in particular under the aspect of the preparation of dental materials from a liquid and a pulverised component. From this explanation, the application of the invention to other components for other application purposes will be readily apparent.

The construction of mixing capsules for dental materials, as are known from the state of the art, is normally as follows. The mixing capsule comprises a hollow piston in which a plunger is guided, the hollow piston typically containing a liquid substance. A mixing chamber usually contains a pulverised substance, with a foil which can be ruptured separating the liquid substance in the hollow piston from the pulverised substance in the mixing chamber. Pushing down the plunger will rupture the foil so that the liquid substance is pressed out of the hollow piston and enters the mixing chamber where it comes into contact with the pulverised substance. The two components are subsequently thoroughly mixed with the aid of mechanical mixing apparatuses. After the components have been mixed in this manner, the plunger is pressed further into the mixing chamber carrying the hollow piston with it. Thereby the mixed mass is pressed out of the mixing chamber through an ejection aperture. In the storage condition before use, air or an inert gas is contained in addition to the pulverised substance in the mixing chamber. This air or gas is distributed throughout the mixed mass during the mixing operation in the form of small air bubbles or vacuoles. As a result, the porosity of a dental material made from the mixed mass increases. This makes it difficult to prepare polishable smooth surfaces of dentures, which are desirable under medical and aesthetic aspects. The presence of vacuoles or small air bubbles in the mixed substance further leads to a reduction of the strength of a dental material made from the mixed substance.

The invention is based on the object to provide a mixing device for several components, by means of which mixtures containing a reduced proportion of vacuoles and air bubbles can be prepared.

This object is met by a mixing device as specified in claim 1. Advantageous developments result from the dependent claims.

The device according to the invention provides for the first chamber in which a first component, preferably a powder, is contained and in which a mixing of the components takes place, to be evacuated. The second chamber containing another component, preferably a liquid, is also essentially free of gas. The device according to the invention has the advantage that no air is present in the system, which might lead to the formation of small air bubbles or vacuoles during the mixing operation of the components. It is thus possible to reproducibly obtain materials such as e.g. dental materials with reduced porosity. It is further advantageous in that the components are protected against oxidation reactions. Another advantage of the device according to the invention is that due to the vacuum suction effect as faster and more homogeneous moistening of a first pulverised component with a second liquid component is possible.

According to a preferred embodiment of the invention it is provided that a porous gas-permeable filter or a porous gas-permeable foil is disposed in an evacuation opening. The filter or the foil may consist of any material, provided that the filter or the foil is gas-permeable, in particular, air-permeable and that it has a sufficiently small pore size so that the first component, in particular a solid material in pulverised or granular form is not drawn from the first chamber by an applied vacuum. The first chamber is usually connected with a vacuum source and evacuated via the evacuation opening, after having been filled with the first component. Subsequently, the evacuation opening is sealed so as to be airtight by means of suitable means, such as e.g. a plug and the like. The evacuation opening of the first chamber may be provided in the face or in the circumference of the outer hollow body (preferably a hollow cylinder) which defines the first chamber.

According to another preferred embodiment, the mixing device is accommodated in a vacuum packing. Particularly preferred, the vacuum packing around the evacuation opening is welded to an outer wall of a body in which the first chamber is formed. A part of the vacuum packing serves in this arrangement as a sealing means (vacuum seal) for the evacuation opening. Thus, no separate component is required for sealing the evacuation opening. The vacuum seal is preferably surrounded by a rated rupture line, so that upon opening the vacuum packing after severing the rupture line the vacuum seal only, i.e. the portion of the vacuum packing which serves as a sealing means of the evacuation opening, remains on the outer wall of the mixing devices. According to a preferred embodiment, the vacuum seal is arranged concentrically about the evacuation hole.

The components accommodated in the first chamber and in the second chamber comprise both liquids and solid substances, preferably in a pulverised form, granular form, or in the form of precompacted solid substances, such as e.g. tablets. Paste-like substances are also possible. The solid substances comprise any non-biological or biological masses, such as e.g. ceramic materials, glass materials, quartz powder, $SiO_x$ containing substances, spongiosa granule (mineralised, de-mineralised, or partially mineralised, preferably with granule sizes ranging from 250 μm to 1 mm) and others. As liquids, for example polymerisable materials such as e.g. acrylic, methacrylic, or maleic acid derivatives containing poly acids, electrolytic solutions, and others may be considered. The invention also covers the use of one or several further components which may be introduced via a septum arranged on the device. Said component or components respectively, may e.g. be a solution containing a medicine.

The body of the mixing device as well as the piston and the plunger may e.g. consist of synthetic materials, such as PE, PP, PET, PTFE, PVC, EVA, or polyamides. If necessary, they may be vapour deposited or coated with metals or other materials. They may also be formed from metals, glass, or ceramic materials. When using synthetic materials, the components may be manufactured by an injection moulding method. The ejection aperture of the mixing device is preferably designed closable, snout displacement caps or pivotally supported discharge spouts being employed.

The divider means preferably comprises a single- or multi-layer foil, if required a compound foil or a sealing foil. The foil may consist of aluminium and/or synthetic material. PE, PP, PET, PTFE, PVC, and polyamides, for example, are suitable as synthetic materials. The foil is attached e.g. by hot sealing, gluing, ultrasonic or high-frequency welding to the plate provided with an opening, in order to ensure the proper isolation of the first component from the second component, and in order to prevent the second component from being drawn through the foil upon the evacuation of the first chamber, the foil must not be permeable for the liquid or its gases.

The mixing device according to the invention may be sterilised by commonly employed techniques, e.g. by treatment with ionising radiation and others. A sterilisation of the mixing device may also be performed after it has been packaged into a vacuum packing. According to another embodiment, the various chambers with their respective components may also be sterilised by different techniques. Insertion of the plunger into the body of the mixing device upon an activation of the mixing device may be effected manually or by means of suitable tools.

According to a preferred embodiment of the mixing device of the invention, the divider means separating the first from the second chamber comprises a foil and a plate provided with an opening. The foil preferably has such a shape and elasticity and adheres with such a strength to the plate that it opens up a flow cross-section for the component, in particular a liquid, without rupturing when the plunger is axially moved in the hollow cylinder. Such a divider means may be installed both into the above described mixing device evacuated according to the invention and into any mixing device of the state of the art.

The advantage compared to conventional foils is that the foil does not get torn off and no fragments of the foil can enter the mixed mass. By the inventive suitable selection of foil shape, foil elasticity, and cohesion strength of the foil to the plate, only a flow cross-section for the component, in particular a liquid, is opened up without enabling fragments of the foil to be torn off.

It is crucial here that the cohesion of the foil to the plate is smaller than the rupture strength of the foil material. This ensures that the foil slightly lifts off at the site with the weakest cohesion and the liquid is allowed to flow out. The foil may be provided in a plurality of various shapes, but it is decisive that one site represents some kind of 'rated break point', i.e. a site with a weaker cohesion of which it is ensured that it opens and allows the liquid to escape. This can be achieved in that a symmetric base comprises a recess at one site. The foil preferably comprises a circular basic shape with a recess. According to an alternative embodiment, the 'rated break point' can be obtained in that the foil is tacked to the plate less firmly at one site by means of suitable techniques.

The divider means is preferably provided in the form of a single or multi-layer foil, preferably of aluminium and/or synthetic material. PE, PP, PET, PTFE, PVC, and polyamides, for example, are suitable as synthetic materials. The foil is attached e.g. by hot sealing, gluing, ultrasonic or high-frequency welding to the plate which is provided with an opening.

According to another preferred embodiment of the invention, the mixing device comprises a plunger which is movably guided in an inner hollow cylinder and comprises a rounded face and/or consists of an elastic material. Such a plunger may be installed both into the above described mixing device evacuated according to the invention and into any mixing device of the state of the art.

A state of the art divider means is known from EP 1 334 550 A1, in which a hollow cylinder with a perforated wall in its lower portion is designed in such a manner that the perforated wall of the hollow cylinder at its outer surface is closed by means of a foil and a perforated disk between which and the perforated wall the foil is sandwiched. Upon the activation of the plunger accommodated in the hollow cylinder, the liquid component in the hollow cylinder is compressed and the foil ruptures under a certain pressure and allows the liquid component to escape. With this construction, a certain dead volume will invariably occur in the area from perforated wall to perforated disk.

The advantage of using a plunger with a rounded face and a divider means sealing the second face of the hollow cylinder, which on the side facing the inside of the hollow cylinder comprises a rounded surface in order to accommodate the rounded face of the plunger in a perfect fit, is that with this construction no dead volume will occur in the chamber for the liquid. It is thus possible to achieve a high metering accuracy of the liquid component. This is reproducible and will also be obtained with low-viscosity components such as electrolytic liquids.

According to a preferred embodiment, the plunger has a ball-shaped face, and the divider means has a semi-spherical structure on its side facing the inside of the hollow cylinder, which is adapted to accommodate the plunger with a perfect fit.

In a further embodiment, the plunger is formed from an elastic material. This allows a filling method for the hollow cylinder with a liquid without gas bubbles. The hollow cylinder is sealed with a foil which is tacked to a plate provided with a hole. Subsequently, the liquid is filled in followed by the insertion of the plunger. The latter is compressed in radial direction, which is enabled only thanks to the elastic material, whereby gas (air) which has accumulated above the liquid level may escape laterally past the plunger. The pressure acting on the plunger is then released again. This method permits the filling of the chamber of the hollow cylinder with a liquid without gas bubbles and without affecting the adhesion of the foil at the plate by liquid residuals. Alternatively, the hollow cylinder may be filled with a liquid by first inserting the plunger and then introducing the liquid through the opening in the plate of the hollow cylinder's lower part. After this, the chamber is sealed by attaching the foil to the plate. In this instance, however, adhesion between the foil and the plate may be impaired because of liquid residuals on the plate.

The plunger may be made from caoutchouc or a thermoplastic elastomer. The plunger's diameter may be larger than the inner diameter of the hollow cylinder, if required, provided the plunger can be inserted into the hollow cylinder.

The invention further comprises a method of vacuum packaging a mixing device according to the invention, in which the first chamber of the mixing device and the packing are evacuated in one step by connecting them to a vacuum source.

According to a preferred embodiment, the mixing device is first inserted into a suitable packing and this is sealed at three sides. Subsequently, the vacuum source is connected to the fourth open side of the packing, so that the packing can be evacuated. In addition, the first chamber is evacuated via the evacuation opening. The subsequent sealing of the fourth side of the packing produces the vacuum packaged mixing device. An advantage of this method is that the mixing device can be evacuated and vacuum packaged very easily and rapidly. This process is therefore a very efficient method of vacuum packaging the mixing device according to the invention.

As vacuum packings and vacuum sources those known from the state of the art may be used.

According to a preferred embodiment of the method according to the invention, it comprises the additional step of welding the vacuum packing around the evacuation opening to an outer wall of the body in which the first chamber is formed. Thus, a portion of the vacuum packing serves as a sealing means for the evacuation opening. When opening the vacuum packing, the packing (vacuum seal) remains adhered to the welded portion at the mixing device. This ensures that no air enters the chamber within the outer hollow body even after the vacuum packing has been opened. In addition, no separate component for sealing the evacuation opening is required.

The vacuum seal is preferably surrounded by a rated rupture line so that upon opening the vacuum packing after severing the rupture line, only the vacuum seal as the portion of the vacuum packing serving as sealing means for the evacuation opening remains on the outer wall of the mixing device. This considerably facilitates handling of the mixing device during the mixing operation compared to a configuration in which the entire packing remains on the mixing device. According to a preferred embodiment, the vacuum seal is disposed concentrically about the evacuation opening.

Preferred exemplary embodiments of the mixing device will be explained below with reference to the drawing.

FIG. 1 shows in the upper part of the illustration a side view, in the lower part of the illustration a longitudinal section of a mixing device in disassembled condition;

FIG. 2 shows a longitudinal section of the mixing device illustrated in FIG. 1 in assembled condition;

FIG. 3 shows a longitudinal section of the mixing device illustrated in FIG. 1 with a vacuum packing;

FIGS. 4A-4B show a component with a plunger and a hollow cylinder in disassembled condition;

FIG. 5 shows the component illustrated in FIG. 4 in assembled condition;

FIGS. 6A-6B show a front view of a divider means.

According to FIGS. 1 to 3, the mixing device comprises a hollow body 2 which at its first face has an end wall 3, and into whose second face an inner hollow cylinder 10 is inserted. In the end wall 3 an outlet opening 4 is formed coaxially with a longitudinal axis of the hollow cylinders 2, 10. The outlet opening 4 may be closed by means of a plug or the like (not shown). The outer hollow body 2 includes a first chamber 1. In the hollow cylinder 10 a second chamber 12 is formed. The outer hollow body 2 comprises an evacuation opening 5 for the first chamber 1. The inner hollow cylinder 10 is open at its first face and comprises a plate 11 provided with an opening 11a at a second face. A plunger 20 is guided so as to be axially slidable in the inner hollow cylinder 10. The opening of the plate 11 is sealed with a foil 13, in particular of aluminium or synthetic material. The foil 13 is disposed on the side of the plate 11 facing the first chamber 1.

For filling the mixing device, the foil 13 is first attached to the plate 11 by gluing, welding, or sealing. A powder or granules as the first component is filled into the first chamber 1. With the perforated plate 11 directed downwards, a second component, in particular a liquid component, is filled into the second chamber 12. Then the second chamber 12 in the inner hollow cylinder 10 is closed by means of the plunger 20. The latter may be formed in particular from a thermoplastic elastomer in such a manner that it can be compressed radially in order to have gas which has accumulated above the liquid level escape laterally past the plunger 20. The pressure acting on the plunger 20 is subsequently released again. A pin (not shown) may, for example, be arranged between the plunger and the inner wall of the second chamber during insertion of the plunger and then removed. The liquid may also be introduced in that first the plunger 20 is inserted into the inner hollow cylinder 10. With the perforated plate 11 directed upwards, the liquid component is then filled into the second chamber 12. Subsequently, the foil 13 is attached to the plate 11 provided with an opening 11a as has been described above.

Then the inner hollow cylinder 10 is inserted into the outer hollow body 2. The configuration shown in FIG. 2 is obtained in this manner.

Subsequently, the evacuation opening 5 is connected with a vacuum source (not shown), in particular with a vacuum pump. A porous gas-permeable filter or a porous gas-permeable foil 6 is arranged in the evacuation opening 5. The filter or the foil may consist of any material which is gas-permeable, in particular air-permeable, and has a sufficiently small pore size, so that the first component is not drawn from the first chamber 1 by a vacuum applied to the opening 5. After the evacuation, the evacuation opening 5 is sealed airtight with suitable means (not shown) such as, e.g. a plug or the like. The evacuation opening of the first chamber 1 may be formed in the end wall 3 or in the circumference (illustrated arrangement) of the outer hollow body 2 defining the first chamber 1.

For use of the mixing device, the plunger 20 is urged axially into the inner hollow cylinder 10. This may be done either manually or by means of a tool (not shown). Thereby the liquid is compressed and presses against the foil 13 until it releases a flow cross-section and allows the liquid to enter the first chamber 1. The mixing device is then introduced into a vibratory mixer and the plunger 20 is pressed further in axial direction towards the end wall 3, either manually or by means of an appropriate tool, after the mixing. This causes the inner hollow cylinder 10, too, to be pressed towards the end wall 3 so that the mixed substance can exit the outlet opening 4.

FIG. 3 shows a mixing device according to FIGS. 1 and 2 in a vacuum packing 30. The vacuum packing 30 formed by the foil comprises a weld or seal seam 31 around the mixing device, which ensures an airtight packing. The vacuum packing further comprises a tear-off tab 34. The evacuation opening 5 of the mixing device is encompassed by a vacuum seal 32. A rated rupture line 33 is arranged around the vacuum seal. This allows to open the packing 30 and to tear it off at the rated rupture line. Thus, only a small portion of the packing 30, i.e. the vacuum seal 32, remains on the mixing device. This maintains the vacuum in the first chamber 1.

FIG. 4 shows a hollow cylinder 10 with a plate 11 with a rounded surface 14 (FIG. 4A) as well as a plunger 20 with a complementary rounded face 21 (FIG. 4B). FIG. 5 is an illustration of the assembled component consisting of the hollow cylinder 10 with the plunger 20 in activated condition, i.e. after the discharge of the liquid component from the second chamber 12. The advantage of using a plunger 20 with a rounded (crowned) face 21 and a plate 11 which has a rounded surface 14 on its side facing the inside of the inner hollow cylinder 10 and which is suited to accommodate the rounded face 21 of the plunger 20 in a perfect fit is that with this construction no dead volume occurs in the second chamber 12 for the liquid, as can be seen from FIG. 5. According to a preferred embodiment, the plunger 20 is formed from an elastic material such as e.g. caoutchouc or a thermoplastic elastomer. This enables the plunger 20 to be compressed in radial direction during filling of the hollow cylinder 10 so that the gas which has accumulated above the liquid level may escape laterally past the plunger 20. The pressure acting on the plunger 20 is subsequently released again. The second chamber 12 therefore contains only a liquid, but no gas.

FIG. 6 shows a plan view of a divider means with the foil 13 (FIG. 6A) as well as with the plate 11 provided with the opening, on which the foil 13 is secured (FIG. 6B). The foil 13 preferably consisting of aluminium or polyethylene is to have such a shape and elasticity and to adhere with such a strength that it releases a flow cross-section for the component, in particular a liquid, when the plunger 20 is moved axially in the inner hollow cylinder 10, without rupturing the foil 13. This means that the cohesion of the foil 13 at the plate 11 is to be weaker than the rupture strength of the foil material. This ensures that the foil slightly lifts off at the site with the weakest cohesion and the liquid is allowed to flow out. The foil 13 in FIG. 6 comprises a preferred shape for this purpose, i.e. a circular basic shape with a recess (35). FIG. 6B also shows seal seams (36) for attaching the foil 13 to the plate 11. The foil 13 may be attached to the plate 11 provided with a central opening 11a by e.g. hot sealing, gluing, ultrasonic or high-frequency welding.

The invention claimed is:

1. A mixing device with a first chamber (1) for a first component, a second chamber (12) for a second component, and a divider means (11, 13) separating the first and the second chamber, in which the second chamber (12) is defined by an inner hollow cylinder (10) which is arranged so as to be movable in a piston-like fashion in an outer hollow body (2) including the first chamber (1), and the first chamber comprises an evacuation opening (5) that is adapted to be connected with a vacuum source, characterized in that a vacuum packing (30) is welded around the evacuation opening (5) of the first chamber to the outer hollow body (2).

2. The mixing device according to claim 1, characterised in that the dividing means (13) closing a fluid connection between a first and a second chamber releases, by compression of the fluid, a flow cross-section through which fluid can penetrate from the second chamber into the first chamber.

3. The mixing device according to claim 1, characterised in that a porous gas-permeable filter (6) or a porous gas-permeable foil is disposed in the evacuation opening (5).

4. The mixing device according to claim 1, characterised in that the first component is a solid material in the form of powder, granules, or tablets and the second component is a liquid.

5. The mixing device according to claim 1, characterised in that a plunger (20) is accommodated in the inner hollow cylinder (10).

6. The mixing device according to claim 1, characterised in that the divider means (11, 13) comprises a plate (11) which defines the second chamber (12) and is provided with an opening (11a), and a foil (13) which is attached to the plate (11), the foil (13) having such a shape and elasticity and adhering with such a strength that it releases a flow cross-section for the first component, in particular a liquid, without rupturing when the plunger (20) is axially moved in the inner hollow cylinder (10).

7. The mixing device according to claim 1, characterised in that the divider means (11, 13) comprises a plate (11) which defines the second chamber (12) and is provided with an opening (11a), and a foil (13) which is attached to the plate (11), the foil (13) having such a shape and elasticity and adhering with such a strength that it releases a flow cross-section for the first component, in particular a liquid, without rupturing when the plunger (20) is axially moved in the inner hollow cylinder (10) and the foil (13) having a circular basic shape with a recess (35).

8. The mixing device according to claim 1, wherein the divider means (11, 13) comprises a plate (11) which defines the second chamber (12) and is provided with an opening (11a), and a foil (13) which is attached to the plate (11), the foil (13) having such a shape and elasticity and adhering with such a strength that it releases a flow cross-section for the first component, in particular a liquid, without rupturing when the plunger (20) is axially moved in the inner hollow cylinder (10), and the foil (13) being an aluminium foil or a foil of synthetic material.

9. The mixing device according to claim 6, characterised in that the plunger (20) comprises a rounded face (21).

10. The mixing device according to claim 1, characterised in that the divider means (11, 13) comprises a rounded surface (14) at its side facing the inside of the inner hollow cylinder (10), in order to accommodate the rounded face (21) of the plunger (20) with perfect fit.

11. The mixing device according to claim 9 wherein the plunger is formed from an elastic material.

12. The mixing device according to claim 6, characterized in that the plunger is formed from an elastic material.

* * * * *